United States Patent [19]

Metz

[11] Patent Number: 5,403,918
[45] Date of Patent: Apr. 4, 1995

[54] FATTY ACYL REDUCTASE

[75] Inventor: James G. Metz, Woodland, Calif.

[73] Assignee: Calgene, Inc., Davis, Calif.

[21] Appl. No.: 767,251

[22] Filed: Sep. 27, 1991

Related U.S. Application Data

[63] Continuation-in-part of Ser. No. 659,975, Feb. 22, 1991, abandoned.

[51] Int. Cl.$^6$ .......... C07K 15/10; C07K 3/28; C12N 9/02
[52] U.S. Cl. .................. 530/379; 435/189; 530/344
[58] Field of Search ............ 435/189, 183; 530/379, 530/344

[56] References Cited

PUBLICATIONS

Ohlrugge, J. B. et al. Lipids, vol. 13 (1978) pp. 203–210.
Kolattukudy, P. E., et al. Methods in Enzymology, vol. 71 (1981) pp. 263–275.
van Renswoude, J., et al. Methods in Enzymology, vol. 104 (1984) pp. 329–339.
Pollard, et al., "Studies on Biosynthesis of Waxes by Developing Jojoba Seed. II. The Demonstration of Wax Biosynthesis by Cell-Free Homogenates," *Lipids* (1979) 14:651–662.
Wu, et al., "Studies of Biosynthesis of Waxees by Developing Jojoba Seed: III. Biosynthesis of Wax Esters from Acyl-CoA and Long Chain Alcohols," *Lipids* (1981) 16:897–702.
Karplus, et al., "Atomic Structure of Ferredoxin-NADP+ Reductase: Prototype for a Structurally Novel Flavoenzyme Family," *Science* (1991) 251:60–66.
Wildner and Hallick, "Wax Ester Biosynthesis in *Euglena gracilis*," abstract from *The Southwest Consortium on Plant Genetics and Water Resources Fifth Annual Meeting,* Apr. 22–24, 1990, Las Cruces, NM.
Pushnik, et al., "Characterization of the Biosynthetic Pathway For Formation of Liquid Wax in Jojoba," abstract from *The Southwest Consortium on Plant Genetics and Water Resources Fourth Annual Meeting,* Feb. 7, 1989, Riverside, Calif.
Kolattukudy, et al., "Acyl-CoA Reductase and Acyl-CoA: Fatty Alcohol Acyl Transferase In The Microsomal Preparation From The Bovine Meibomian Gland," *Journal of Lipid Research* (1986) 27:404–411.

*Primary Examiner*—David T. Fox
*Assistant Examiner*—Charles Rories

[57] ABSTRACT

By this invention, a partially purified seed-plant fatty acyl reductase protein is provided, wherein said protein is active in the formation of a fatty alcohol from a fatty acyl substrate. Of special interest are jojoba embryo reductase proteins having molecular mass of about 54 and 52 kD and sequences obtainable therefrom. Also considered are amino acid and nucleic acid sequences obtainable from such fatty acyl reductases.

3 Claims, No Drawings

FATTY ACYL REDUCTASE

This application is a continuation-in-part of U.S. Ser. No. 07/659,975, Feb. 22, 1991, now abandoned.

TECHNICAL FIELD

The present invention is directed to plant enzymes, methods to purify, and obtain such enzymes, amino acid and nucleic acid sequences related thereto, and methods of use for such compositions.

INTRODUCTION

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bands. As the carbon chain of fatty acyl molecules always contains an even number of carbons, the formula "$C_{2x}$" may also be used to represent carbon chain length.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

Many plants have been studied which store lipid as triacylglycerols composed primarily of long chain (having 16 or 18 carbons) fatty acyl groups. Very long chain (having 20-24 carbons) monounsaturated fatty acyl groups are formed by an acyl-CoA elongation pathway from C18:1 and are found in many plant seeds, notably members of the Crucifereae family. The desert shrub, *Simmondsia chinensis*, better known as jojoba, is unique among higher plants (seed-bearing plants) in its ability to produce and store large amounts of liquid wax as the major component of its seed storage lipid. These simple wax compounds are oxygen esters of very long-chain monoenoic fatty acyl groups and alcohols.

Other types of waxes are formed by some plant species. The synthesis of plant epidermal, or cuticular wax, as well as wax synthesis by bacteria, such as *Acinetobacter* (Fixter et al. (1986) *J. Gen. Microbiol.* 132:3147-3157) and *Micrococcus* (Lloyd (1987) *Microbios* 52:29-37), and by the unicellular green algae, Euglena, are well known. However, the composition and biosynthetic pathway of these waxes differs from the jojoba seed wax.

In the formation of Euglena storage wax for instance, it has been demonstrated that the alcohol portion is formed by an NADH-dependent reduction of a fatty acyl compound catalyzed by a fatty acyl-CoA reductase. In jojoba seeds, the reaction is NADPH-dependent. It has been postulated that the reduction of a very long chain fatty acyl-CoA to the corresponding alcohol is dependent upon a single enzyme whose activity has been observed in crude extracts from developing jojoba seeds (Pollard et al. (1979) *Lipids* 14:651-662; Wu et al. (1981) *Lipids* 6:897-902). Also, by comparison, for the formation of plant cuticular waxes, a two step process has been reported (Kolattukudy (1980) in *The Biochemistry of Plants* (Stumpf, P. K. and Conn, E. E., eds.) Vol.4, p. 571-645). The fatty acyl-CoA is converted to a free aldehyde by the action of an NADH-dependent reductase and the alcohol is subsequently formed by the action of an NADPH-dependent fatty aldehyde reductase.

Further characterization of the enzymes responsible for formation of wax esters in plants has been hindered by the lack of protocols which result in the identification of polypeptides associated with the enyzmatic activity. It is desirable, therefore, for further study of plant fatty acyl reductase proteins to devise a purification protocol whereby the reductase polypeptide(s) can be identified. By establishing these methods, sufficient amounts of plant fatty acyl reductase protein may be obtained, the amino acid sequence of the protein may be determined and/or antibodies specific for the fatty acyl reductase may be obtained. The resulting amino acid sequences may be useful in polymerase chain reaction (PCR) techniques or for screening cDNA or genomic libraries. Alternatively, antibodies may be used for screening expression libraries to identify clones expressing fatty acyl reductase protein. Clones obtained in this manner can be analyzed so that the nucleic acid sequences corresponding to plant fatty acyl reductase are identified.

Relevant Literature

Cell-free homogenates from developing jojoba embryos were reported to have NADPH-dependent fatty acyl-CoA reductase activity. The activity was associated with a floating wax pad which formed upon differential centrifugation (Pollard et al. (1979) supra; Wu et al. (1981) supra).

Conservation of functional residues in known dinucleotide binding folds of several reductase proteins is presented by Karplus et al. (*Science* (1991) 251:60-66).

Solubilization of a multienzyme complex from *Euglena gracilis* having fatty acyl-CoA reductase activity is reported by Wildner and Hallick (Abstract from *The Southwest Consortium Fifty Annual Meeting*, Apr. 22-14, 1990, Las Cruces, N. Mex.

3000-fold purification of jojoba reductase protein is reported by Pushnik et al. (Abstract from *The Southwewst Consortium Fourth Annual Meeting*, Feb. 7, 1989, Riverside, Calif.).

SUMMARY OF THE INVENTION

By this invention, a partially purified fatty acyl reductase protein is provided, wherein said protein is active in the formation of a fatty alcohol from a fatty acyl substrate. The reductase of this invention may be active with a variety of fatty acyl substrates, including acyl-CoAs and acyl-ACPs. The carbon chain length of these substrates may vary, although a given reductase may show preference for a specific chain length acyl substrate or may be active with acyl substrates having a wide range with respect to carbon chain length.

In general, the reductase of this invention has activity towards at least those acyl substrates having a chain length of from 16 to 24 carbons, which carbon chain length may be represented by the formula "$C_{2x}$", where "x" is a number from 8 to 12, although other acyl substrates may be tested and further activities discovered. In addition, having obtained the reductase protein of this invention, further manipulations are now possible as described in further detail below. These manipulations may lead to production or discovery of other related reductases.

Thus, in a first aspect, this invention relates to protein preparations demonstrating fatty acyl reductase enzymatic activity, and is exemplified by a seed-plant protein preparation. Such a preparation is produced by fractionation of jojoba embryos to produce a microsomal membrane preparation, solubilization of the reductase protein from this membrane preparation and further purification by chromatographic procedures. The jojoba reductase is shown to prefer very long chain acyl-CoA substrates, although activity with other acyl substrates is also observed, and is confirmed to be NADPH-dependent.

By these procedures, a partially purified reductase preparation is obtained which contains two prominent polypeptides which migrate as a doublet band on polyacrylamide gels, and which have apparent molecular masses of approximately 54 and 52 kD. Thus, methods of obtaining acyl reductase proteins through purification from seed-plant sources are provided, as well as methods to obtain amino acid sequences of these reductase proteins.

In a different aspect of this invention, nucleic acid sequences associated with a reductase of this invention are considered. Methods are described whereby these sequences may be identified and obtained from the amino acid sequences of the reductase proteins of this invention. Uses of the structural gene sequences for isolation of other reductase sequences, as well as in recombinant constructs for transcription of reductase nucleic acid sequences and/or expression of reductase proteins in host cells are described. Uses of other nucleic acid sequences associated with reductase protein are also considered, such as the use of 5' and 3' noncoding regions.

In yet a different aspect of this invention, cells containing the recombinant constructs of this invention are considered. In particular, cells which contain the preferred substrates of a jojoba reductase, such as those cells in embryos of Brassica plants, are considered.

In addition, cells containing the reductase protein of this invention as the result of expression from the recombinant constructs of this invention are considered, and a method of producing a reductase in a host cell is provided. Accordingly, a reductase protein that is recovered as the result of expression of that protein in a host cell is also considered in this invention. Further, it may be recognized that the reductases of this invention may find application in the production of fatty alcohols in such host cells.

DETAILED DESCRIPTION OF THE INVENTION

A fatty acyl reductase of this invention includes any sequence of amino acids, such as protein, polypeptide or peptide fragment, which is active in catalyzing the reduction of a fatty acyl group to the corresponding alcohol. By fatty acyl group is intended any fatty acyl group, covalently bound to a carrier, such as ACP or coenzyme A.

Other enzymes may or may not be required for the reduction of the fatty acyl group to the alcohol, as this enzymatic reaction involves a 4 electron reduction which may be carried out in two steps. In the first step, the acyl group may be converted to an aldehyde, which would then be reduced to the corresponding alcohol. Thus, the reductase of this invention may be active through the entire 4 electron reduction, from acyl to alcohol, or may catalyze the reduction to the aldehyde, which is then further reduced to the alcohol by a second enzyme. Evidence obtained thus far indicates a single enzyme carries out the complete reduction of acyl CoA to alcohol. The fatty acyl reductase of this invention is also referred to hereafter as "acyl reductase" or "reductase".

Thus, this invention relates to seed-plant fatty acyl reductases which convert fatty acyl groups to alcohols. More particularly, this invention relates to NADPH-dependent reductases. In addition, it is noted that a plant fatty acyl reductase of this invention may have activity towards both fatty acyl-CoA or fatty acyl-ACP molecules, and the activity observed may depend upon the substrate available. However, preferential activity toward very long chain acyl-CoA substrates is desired for manipulation of the fatty acid synthetase (FAS) acyl-CoA elongation pathway.

By this invention, it has been determined that the seedplant fatty acyl reductase protein is an integral membrane protein. In general, membrane associated proteins are difficult to purify as they tend to lose enzymatic activity when they are solubilized, i.e. separated from the membrane environment in which they normally function. However, obtaining a solubilized seed-plant fatty acyl reductase which still retains its enzymatic activity can permit various uses which are not possible with a membrane-bound protein.

For example, once a purified or partially purified acyl reductase protein is obtained, it may be immobilized and used in a reactor system to prepare fatty alcohols in the presence of a reduced pyridine nucleotide regenerating system. Further, study of the reductase protein may lead to site-specific mutagenesis studies to further characterize and improve its catalytic properties or to alter its acyl substrate specificity. A reductase with altered substrate specificity may find application in conjunction with other FAS enzymes. For example, a medium chain (C12-14) preferring plant thioesterase (see copending U.S. patent application Ser. No. 07/662,007), and an appropriate acyl transferase may be used in conjunction with an altered reductase to produce medium-chain alcohols, which may then be esterified to fatty acids to yield esters.

One significant factor to be considered when working with membrane bound proteins is the extent of the association of the protein with the membrane. Both peripheral and integral membrane proteins are known. Peripheral proteins are typically somewhat hydrophilic in nature, only loosely associated with the membranes and easily solubilized. Integral proteins, on the contrary, have highly hydrophobic regions embedded in the lipid membrane and often must be associated with lipids if they are to retain enzymatic activity.

Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized protein preparation a microsomal membrane preparation of seed-plant tissue which comprises acyl reductase activity is desired. Standard microsomal membrane preparations utilize differential centrifugation of a cell-free homogenate (CFH) to yield a membrane fraction which is free of whole cells, nuclei and soluble protein. (See, for example Mooré et al. (1987) *Biological Membranes: A Practical Approach*, pp. 37–72, eds. Finalay and Evans.) With oilseed, initial centrifugation steps typically yield a pellet, supernatant and a floating fat pad, and microsomal members may then be recovered by further centrifugation of the supernatant.

A protocol has been described in co-pending U.S. Ser. No. 07/659,975, filed Feb. 22, 1991, now abandoned, whereby a membrane fraction containing active acyl reductase protein was obtained with good recovery of reductase activity relative to that in the CFH. A critical step in this process was the removal of the seed coat from the jojoba embryos as the coats are found to contain a factor(s) that interferes with enzymological measurements. The method employs a high salt solution during the initial portion of the protocol, the steps of which are also described below and in more detail in the examples which follow.

A powder is produced from a jojoba embryo sample, and a homogenate is prepared by homogenizing the powder in a high salt (3M NaCl) sucrose (0.3M) solution at a ratio of 80 ml of solution per 20 gm embryos. The homogenate is then filtered and centrifuged at 100,000× g for approximately one hour, wherein a pellet, supernatant and a floating fat pad are obtained. The fat pad is removed and the supernatant is collected and dialyzed against a 1M NaCl solution which also contains 100 mM HEPES (pH 7.5), 2 mM DTT and 0.5 mM EDTA. The dialyzate is then centrifuged at 100,000× g, or more preferably at 200,000× g for approximately one hour, wherein a pellet, DP2, is obtained which comprises microsomal membranes having acyl-CoA reductase activity.

Further characterization of the acyl reductase activity in the microsomal membrane preparation and during further purification procedures may be facilitated by developing an optimized specific assay for the acyl reductase. For example, with jojoba an assay is employed which utilizes very long chain acyl-CoA molecules as substrates and which is conducted under high salt (0.2M to 0.5M NaCl) conditions, high salt having been found to significantly increase the detectable acyl-CoA reductase activity. This assay is described in detail in Example 1.

Another critical stage for further enzyme characterization and purification is that of obtaining solubilized reductase protein that is separated from its native lipid bilayer membrane environment, but retains substantial amounts of measurable reductase enzymatic activity. The removal of integral membrane proteins from the lipid bilayer is typically accomplished using amphiphilic detergents in aqueous solution, although organic solvents have also been used in a few cases. Many different detergents are available, both ionic and nonionic, which vary in their dissociating effects, critical micelle concentration (CMC), effect on enzymatic activity and further purification, and ease of removability from the solution. Many different detergents and methods of solubilization of membrane proteins are known to those skilled in the art, and are also reviewed by Neugebauer (*Methods Enzymol.* (1990) 182:239–253) and Hjelmiland (*Methods Enzymol.* (1990) 182:253–264).

Often, detergents which are used to solubilize membrane proteins are found to inhibit the enzymatic activity of a desired protein. Several detergents were tested for solubilization of jojoba acyl reductase, representing a wide range of characteristics, and all were found to be inhibitory. However, as apparent detergent inhibition of reductase activity may be due to some effect other than irreversible inhibition of the enzyme, the reversibility of inhibition by CHAPS was examined.

Although strong inhibition by the detergent CHAPS (3-[(3-cholamidopropyl)-dimethyl-ammonio]-1-propanesulfonate) at concentrations above the CMC was seen, it was found that if the enzyme was exposed to CHAPS on ice, and then returned to a CHAPS concentration at or below the CMC value, complete recovery of reductase activity was obtained. Thus, reductase is not irreversibly inhibited by the detergent CHAPS. A protocol for solubilizing jojoba acyl reductase activity utilizing the detergent CHAPS has been devised which yields approximately 85% of the reductase activity from the microsomal membrane preparation. This method is discussed in detail in Example 2. Similarly, studies of reversibility of apparent reductase inhibition by other detergents may be conducted to identify other useful detergents for solubilization of acyl reductase activity for jojoba or other candidate reductases.

Having obtained the solubilized acyl reductase protein, it can be seen that further experiments to characterize the enzyme as to substrate specificity, cofactor requirements and possible activity inhibiting agents may now be conducted. For example, it has been found that the jojoba acyl reductase of this invention has a broad range of substrates, including ACP and CoA substrates. For example, activity towards acyl-ACP substrates having at least 16 carbons is observed, as well as activity towards acyl-CoA substrates having at least 18 carbons. A preferred activity toward [C15]-15-tetracosenoyl-CoA (C24:1) is observed.

Protein preparations may be further enriched for a candidate plant acyl reductase protein, for example by chromatography over an immobilized reactive dye. Many such reactive dye matrices are known, including the Cibacron Blue F3GA (Blue A) used in this invention. By this invention it is demonstrated that jojoba acyl reductase activity binds to such a column when loaded in a buffer containing approximately 0.2M NaCl, and more preferred .5M NaCl, or more preferred 0.4M NaCl, while greater than approximately 85% of other protein passes through or is removed in subsequent washes. Further, it is demonstrated that jojoba acyl activity can be recovered by elution from the Blue A column in a buffer containing approximately 1.0M NaCl.

The acyl reductase activity is further purified by applying the enriched protein preparation from the Blue A column to a column packed with a size exclusion matrix also sometimes called a gel filtration column. The size exclusion column also provides an estimate of the size of the native reductase enzyme. In particular, a narrow range sizing column matrix, such as Ultragel AcA54 or Sephacryl S100, is useful in obtaining further purified jojoba acyl reductase fractions. Of special interest are methods and buffers which may be utilized to obtain recovery, in one main peak, of greater than approximately 40–60% of the reductase activity that is loaded to size exclusion a column or its equivalent.

Application of the reductase activity from a size exclusion column to an affinity column results in further purification of the reductase protein. For example, active fractions may be applied to a palmitoyl CoA agarose column in approximately 0.1M NaCl. Approximately 70% of the reductase activity may then be eluted with a buffer having 15 mM NADPH, a cofactor of the reductase enzyme from jojoba.

Throughout the purification the fractions comprising acyl reductase activity of this invention may be subjected to further techniques, such as SDS polyacrylamide gel electrophoresis and subsequent staining. In this manner, the prominent polypeptide bands in these fractions having reductase activity can be identified. For example, in a partially purified jojoba reductase preparation from a palmitoyl CoA agarose column, two bands representing polypeptides of approximately 53 kD, more particularly polypeptides having a 54 and 52 kD apparent molecular mass are identified which constitute greater than 95% of the protein in the preparation.

As the apparent size of the native reductase enzyme is approximately 49 kD, as demonstrated by size exclusion chromatography herein, these bands do not likely represent two different subunits of one reductase enzyme. Rather, reductase activity is associated with either one or both of these polypeptides. Tests, including anion exchange, dye columns, hexanoyl-CoA affinity columns, gel filtration, heparin columns and thiol interactive chromatography, have failed to yield additional information.

As the jojoba seeds used in this purification are collected from a diverse population of jojoba plants, these polypeptides may represent closely related variants of the same enzyme, i.e. isozymes. Tryptic digestion and amino acid sequence analysis of the two polypeptides, as described herein, may be used to further characterize the 54 and 52 kD bands.

Recovery of substantially purified reductase protein can now be accomplished using a variety of methods. For example, polyacrylamide gels may be run and the proteins transferred to a membrane support, such as nitrocellulose or polyvinylidenedifluoride (PVDF). The sections of these membranes which contain the identified proteins may then be obtained such that the identified proteins are substantially free of other proteins. Using techniques known in the art and also described in the following examples, the proteins may be removed from the membranes and further manipulated such that their amino acid sequences are determined.

For example, amino acid sequence can be determined by sequencing N-terminal amino acid regions from whole protein or by preparing fragments of the desired protein by digestion with the chemical cyanogen bromide, or alternatively by enzymatic cleavage using proteases. Examples of proteases which may be useful include endoproteinase lysC, gluC, AspN and trypsin. The fragments obtained in this manner may then be purified and sequenced in accordance with methods familiar to those skilled in the art.

Further characterization of the 54 and 52 kD candidate polypeptides may be useful, for example, expression of the respective proteins in *E. coli* and subsequent verification of reductase activity. Other testing may include immunological assays, whereby antibodies specific for the candidate protein are prepared and found to inhibit reductase activity in protein preparations.

Moreover, it is desirable to isolate nucleic acid sequences from amino acid sequences determined for the proteins associated with acyl reductase activity, both to confirm the identity of an acyl reductase protein and to provide for transcription of the sequences and/or expression of the protein in host cells, either prokaryotic or eukaryotic. Various manipulations may be necessary for expression of the reductase in cells. For example, the protein if produced at a high level in a prokaryote, such as *E. coli*, may be disruptive or even toxic due to insertion into cell membranes. Low level expression using a weak promoter, thus may be desirable. Alternatively, if a leader peptide is discovered which may be responsible for membrane insertion, constructs may be prepared which contain only those nucleic acid sequences that encode a mature reductase protein. In this manner the reductase protein may be produced in *E. coli* cells. If reductase activity is not detectable in *E. coli*, for example the protein might not be inserted into the membrane bilayer, the presence of the reductase protein in *E. coli* cells may be confirmed by other means, such as using antibody preparations.

As the acyl reductase is a membrane bound protein, it may be desirable to express a candidate protein in a plant cell in order to verify reductase activity. Electroporation or bombardment of plant tissue for transient expression may be useful for this purpose. Ultimately, stable expression of reductase protein in a plant, such as a member of the Brassica genus, which produces substrates recognized by this enzyme, is desired. In this manner, the acyl alcohol products, which have uses in pharmaceuticals, cosmetics, detergents, plastics, and lube oils may be obtained.

The reductase nucleic acids of this invention may be genomic or cDNA and may be isolated from cDNA or genomic libraries or directly from isolated plant DNA. Methods of isolation of gene sequences once a protein is isolated and/or amino acid sequence of the protein is obtained are known to those skilled in the art.

For example, antibodies may be raised to the isolated protein and used to screen expression libraries, thus identifying clones which produce the plant acyl reductase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Acyl reductase nucleic acid sequences of this invention include those corresponding to the jojoba acyl-CoA reductase protein, as well as sequences obtainable from the jojoba protein or nucleic acid sequences. By "corresponding" is meant nucleic acid sequences, either DNA or RNA, including those which encode jojoba acyl reductase protein or a portion thereof, regulatory sequences found 5' or 3' to said encoding sequences which direct the transcription or transcription and translation (expression) of the reductase in jojoba embryos, intron sequences not present in the cDNA, as well as sequences encoding any leader or signal peptide of a precursor reductase protein that may be required for insertion into the endoplasmic reticulum membrane, but is not found in the mature, or processed, acyl reductase enzyme.

By sequences "obtainable" from the jojoba sequence or protein, is intended any nucleic acid sequences associated with a desired fatty acid reductase protein that may be synthesized from the jojoba acyl reductase amino acid sequence, or alternatively identified in a different organism and isolated using jojoba reductase nucleic acid sequences or antibodies prepared against the jojoba reductase protein as probes. In this manner, it can be seen that sequences of other acyl reductases that are isolated from a desired organism using the jojoba sequences, either by nucleic acid hybridization or antigenic methods, may similarly be used to isolate still other acyl reductases. Such reductases which are derived through seed-plant reductases isolated via jojoba reductase are likewise considered "obtainable" herein.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding acyl reductase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding an acyl reductase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba acyl reductase can be prepared by injecting rabbits or mice with the purified protein, such methods of preparing antibodies being well known to those in the art. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba reductase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some available systems have been described by Oberfelder (*Focus* (1989) BRL/Life Technologies, Inc. 11:1–5). When cross-reactivity is observed, genes encoding the related proteins are isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related acyl reductase protein. Other seed-plant fatty acyl reductases may be obtained through the use of these reductases in the same manner as the jojoba reductase was used.

It will be recognized by one of ordinary skill in the art that acyl reductase nucleic acid sequences of this invention may be modified using standard techniques of site specific mutation or PCR, or modification of the sequence may be accomplished in producing a synthetic nucleic acid sequence. These modified sequences are also considered acyl reductase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an acyl reductase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the reductase protein) may be synthesized using codons preferred by a selected host. Host-preferred codons may be determined, for example, from the codons used most frequently in the proteins expressed in a desired host species.

The nucleic acid sequences associated with acyl reductase proteins will find many uses. For example, recombinant constructs can be prepared which can be used as probes or will provide for expression of the acyl reductase protein in host cells. Depending upon the intended use, the constructs may contain the sequence which encodes the entire reductase, or a portion thereof. For example, critical regions of the reductase, such as an active site may be identified. Further constructs containing only a portion of the reductase sequence which encodes the amino acids necessary for a desired reductase activity may thus be prepared.

Expression in host cells which contain preferred substrates of the acyl reductase protein, may allow for production of fatty acyl alcohols from the corresponding fatty acyl substrates. Useful systems for expression of the reductase protein include prokaryotic cells, such as E. coli, yeast cells, and plant cells, both vascular and nonvascular plant cells being desired hosts. In this manner, the reductase protein may be produced. In addition, site-specific mutagenesis of encoding sequences may be used to study the effects of specific mutations on reactive properties of the reductase protein.

Additionally, antisense constructs may be prepared which provide for transcription of a complementary sequence of an acyl reductase encoding sequence or fragment thereof. In this manner, the amount of the reductase protein produced in a target host organism may be reduced.

The DNA sequence encoding an acyl reductase of this invention may be combined with foreign DNA sequences in a variety of ways. By "foreign" DNA sequences is meant any DNA sequence which is not naturally found joined to the reductase, including combinations of DNA sequences from the same organism which are not naturally found joined together. For example, it may be desirable to join sequences encoding a transit peptide to reductase sequences of this invention. In this manner, the reductase may be targeted to a chloroplast where fatty acyl substrates, particularly fatty acyl-ACPs are available.

The DNA sequence encoding an acyl reductase of this invention may be employed in conjunction with all or part of the gene sequences normally associated with the reductase. In its component parts, a DNA sequence encoding reductase is combined in a recombinant construct having, in the 5' to 3' direction of transcription, a transcription initiation control region capable of promoting transcription and translation in a host cell, the nucleic acid sequence encoding reductase and a transcription termination region.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as E. coli, B. subtilis, Sacchromyces cerevisiae, including genes such as beta-galactosidase, T7 polymerase, tryptophan E and the like.

For the most part, the recombinant constructs will involve regulatory regions functional in plants which provide for production of acyl reductase. The open reading frame, coding for the plant reductase or functional fragment thereof will be joined at its 5' end to a transcription initiation regulatory region. Translational initiation regions may also be desirable and may be provided from the 5' non-coding region of the reductase cDNA sequence or from the translational initiation region naturally associated with the transcription initiation region of the construct. Generally, the combination of transcriptional and translational regulatory regions is referred to as a promoter. Numerous promoter regions are available which provide for a wide variety of constitutive or regulatable, e.g., inducible, expression of structural genes in plants.

Among sequences known to be useful in providing for constitutive gene expression in plants are regulatory regions associated with Agrobacterium genes, such as those for nopaline synthase (Nos), mannopine synthase (Mas), or octopine synthase (Ocs), as well as regions coding for expression of viral genes, such as the 35 S and 19 S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the acyl reductase protein is desired in a plant host, the use of all or part of the complete plant acyl reductase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, or enhanced promoters, such as double 35S CaMV promoters, the sequences may be joined together using standard techniques.

For applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/742,834, filed Aug. 8, 1991), and U.S. Ser. No. 07/494,722 filed on or about Mar. 16, 1990 having a title "Novel Sequences Preferentially Expressed In Early Seed Development and Methods Related Thereto", now abandoned, all of which copending applications are incorporated herein by reference. Transcription initiation regions which are preferentially expressed in seed tissue are considered desirable for fatty alcohol production in order to minimize any disruptive or adverse effects of the gene product in other plant parts.

Regulatory transcription termination regions may be provided in recombinant constructs of this invention as well. Transcription termination regions may be provided by the DNA sequence encoding the plant acyl reductase or a convenient transcription termination region derived from a different gene source, especially the transcription termination region which is naturally associated with the transcription initiation region. The transcript termination region will typically contain at least about 0.5 kb, preferably about 1-3 kb of sequence 3' to the structural gene from which the termination region is derived.

Plant expression constructs having a plant acyl reductase as the DNA sequence of interest for expression thereof may be employed with a wide variety of plant life, particularly, plant life which produce very long chain fatty acyl-CoA molecules, such as Brassica, and in particular high erucic acid varieties of rapeseed. Other plants of interest produce desirable substrates, such as medium or long chain fatty acyl molecules, and include but are not limited to rapeseed (Canola varieties), sunflower, safflower, cotton, Cuphea, soybean, peanut, coconut and oil palms, and corn. Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite mating or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

In developing the recombinant construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the different host species into which the expression constructs are introduced, one or more markers may be employed for selection or detection of transformed tissues, where different conditions for selection are used for the different hosts.

When Agrobacterium is utilized for plant transformation, it may be desirable to have the nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode transacting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in E. coli and Agrobacterium, there being broad host range vectors described in the literature. Commonly used is pRK2 or derivatives thereof. See, for example, Ditta, et al., (Proc. Nat. Acad. Sci., U.S.A. (1980) 77:7347-7351) and EPA 0 120 515, which are incorporated herein by reference. Alternatively, one may insert the sequences to be expressed in plant cells into a vector containing separate replication sequences, one of which stabilizes the vector in E. coli, and the other in Agrobacterium. See, for example, McBride and Summerfelt (Plant Mol. Biol. (1990) 14:269-276), wherein the pRiHRI (Jouanin, et al., Mol. Gen. Genet. (1985) 201:370-374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

For transformation of Brassica cells, for example, Agrobacterium transformation methods may be used. One such method is described by Radke et al. (Theor. Appl. Genet. (1988) 75:685-694).

The invention now being generally described, it will be more readily understood by reference to the following examples, which are included for purposes of illustration only and are not intended to limit the invention unless so stated.

EXAMPLES

Example 1

Acyl-CoA Reductase Assays

Methods to assay for acyl-CoA reductase activity in microsomal membrane preparations or solubilized protein preparations are described.

A. Radiolabeled Material

Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C] cyanide with the corresponding alkyl mesylate, followed by the base hydrolysis of the alkyl nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10Ci/mole. Other [1-$^{14}$C] acyl-CoAs, such as [1-$^{14}$C] tetracasenoyl-CoA, were purchased from Amersham (Arlington Heights, Ill.) [1-$^{14}$C] hexadecanal is prepared by the dichromate oxidation of [1-$^{14}$C] hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Reductase Activity in a Microsomal Membrane Preparation

1. Assay 1: Reductase activity in a microsomal membrane preparation is measured by incubation of 20 μM [1-$^{14}$C] acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as refered to hereafter is added from a 1M stock solution adjusted to pH 7.5).

The assay is started by the addition of acyl-CoA substrate and the incubation is carried out at 30° C. for one hour. The assay is terminated by placing the assay tube on ice and immediately adding 0.25 ml isopropanol: acetic acid (5:1 v/v). Unlabeled wax esters (0. mg) and oleyl alcohol (0.1 mg) are added as carriers. The [$^{14}$C] lipids are extracted by the scaled-down protocol of Hara and Radin (*Anal. Biochem.* (1978) 90:420). Six ml of hexane/isopropanol (3:2, v/v) is added to the terminated assay. The sample is vortexed, 2 ml of aqueous sodium sulphate solution (5.5% w/v) is added, and the sample is again vortexed.

2. Assay 2: Reductase activity in a microsomal membrane preparation is measured by incubation of 20 μM [1-$^{14}$C] acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as refered to hereafter is added from a 1M stock solution adjusted to pH 7.5). If it is desired to inhibit an acyl CoA: alcohol acyl transferase activity which is also present in the membrane preparation (and which consumes the product of the reductase reaction), 0.3% w/v CHAPS is included in the assay mixture. This concentration of CHAPS has a minimal effect on the reductase enzyme but completely inhibits the acyl transferase reaction, thus simplifying quantitation of the reductase activity.

The assay is started by the addition of acyl-CoA substrate and the incubation is carried out at 30° C. for one hour. The assay is terminated by placing the assay tube on ice and immediately adding 0.25 ml isopropanol:acetic acid (4:1 v/v). Unlabeled wax esters (25 μg), oleyl alcohol (50 μg), and oleic acid (50 μg) are added as carriers. The [14C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.7% w/v) is added, and the sample is again vortexed.

C. Assay for Solubilized Reductase Activity

For assaying solubilized reductase activity, several changes, including the addition of salt for enzyme activation, are required. The assay buffer for a solubilized reductase assay is as indicated above for the microsomal membrane preparation assay, with the following changes:

a. NaCl is added to a final concentration of between 0.3 and 0.5M,
b. EDTA is included at ∼1 mM, and
c. the enzyme sample to be assayed, which typically contains 0.75% CHAPS, is diluted to ≦0.3% (the CMC for CHAPS is ∼0.5%).

D. Analysis of Assay Products

For analyzing the products of either the microsomal membrane preparation reductase assay or the solubilized reductase assay, two protocols have been developed. One protocol, described below as "extensive assay" is more time-consuming, but yields more highly quantitative results. The other protocol, described below as "quick assay" also provides a measure of reductase activity, but is faster, more convenient, and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of heptane, and an aliquot is assayed for radioactivity by liquid scintillation counting. The remainder of the sample can be used either for TLC analysis of the labeled classes, or for derivatization to cleave the wax esters, and thereby give a measure of total alcohol produced.

For lipid class analysis the sample is applied to a silica TLC plate, and the plate is developed in hexane/diethyl ether/acetic acid (such as 80:20:1 or 70:30:1 v/v/v). The distribution of radioactivity between the lipid classes, largely wax esters (when ligase is present, as in the microsomal membrane preparation assay), free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis.

For cleavage of the wax esters, a scaled down protocol based on the Grignard derivatization protocol of Pina et al. (*Lipids* (1987) 22:358–361) is used. The sample, plus 200 μg of carrier wax esters, is dried down in a glass tube fitted with a teflon-lined screw cap. Dry diethyl ether (0.4 ml), ethyl acetate (3 μl), and 3M ethyl magnesium bromide in diethyl ether (0.1 ml) are added sequentially. The sample is vortexed and allowed to stand at room temperature for at least 2 hours, after which water-saturated diethyl ether is carefully added to destroy excess reagent. Two ml each of 1M HCl and hexane are added and the tube is vortexed. The upper organic phase is washed with water (2×2 ml) and evaporated to dryness in the presence of 50–100 μl of ethanol.

The sample is resuspended in 50–100 μl of hexane and applied to a TLC plate. Both normal and reversed-phase TLC systems have been used for the analysis. Normal phase TLC uses a silica TLC plate, developed with hexane/diethyl ether/acetic acid (70:30:2 v/v/v). The reversed phase system uses C18 plates developed in methanol.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in heptane and spotted on TLC plates and developed and scanned as described for the detailed assay. In this manner the percentage of the total counts which are incorporated into alcohol is determined.

Example 2

Characterization of Jojoba Acyl-CoA Reductase

Methods to obtain jojoba protein preparations having reductase activity and results of studies of this enzymatic activity are presented.

A. Seed Development and Acyl-CoA Reductase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Acyl-CoA reductase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for acyl-CoA reductase activities as measured in either a cell free homogenate or a membrane fraction, indicate a large induction in reductase activity which peaks at approximately 115 days after anthesis. Embryos for enzymology studies were thus harvested between about 90 to 110 days postanthesis, a period when the reductase activity is high, lipid deposition has not reached maximum levels, and the seed coat is easily removed. The highest rate of increase of reductase activity is seen between days 80 and 90 postanthesis. Embryos for cDNA library construction were thus harvested between about 80 to 90 days postanthesis when presumably the rate of synthase of reductase protein would be maximal. Correspondingly, the level of mRNA encoding acyl-CoA reductase would be presumed to be maximal at this stage.

B. Fractionation Studies

Early attempts to fractionate jojoba embryo samples resulted in variable distribution of reductase activity in the fat pad, supernatant and particulate fractions resulting from centrifugation. A large number of treatments to potentially affect the distribution of activity were tested, such as sonication, floatation gradients, and the addition of various agents to the extraction buffer. The inclusion of salts in the extraction buffer resulted in the greatest improvement in recovery of ligase activity in the supernatant fraction upon centrifugation at 100,000× g for one hour. The extraction buffer consists of 3M NaCl, 0.3M sucrose, 100 mM HEPES, 2 mM DTT, and the protease inhibitors, 1 mM EDTA, 0.7 μg/ml leupeptin, 0.5 μg/ml pepstatin and 17 μg/ml phenylmethanesulfonyl fluoride (PMSF).

C. Microsomal Membrane Preparations

Particles having high levels of reductase activity can be obtained from the supernatant fraction described above either by dialysis followed by centrifugation at 100,000× g or by ammonium sulphate fractionation. The dialysis method is described in detail in Example 3. Further analysis of these particles having reductase activity such as density gradient centrifugation, gel permeation chromatography, and protein/phospholipid analysis establishes that these particles represent a membrane fraction. This membrane preparation also has high cytochrome C reductase activity, which activity is used as a marker for endoplasmic reticulum (ER) membranes. These studies thus establish that the reductase protein is associated with membranes.

For ammonium sulphate fractionation, the 100,000× g supernatant is obtained from jojoba embryos essentially as described in Example 3. An equal volume of ammonium sulphate solution (33.2 g/100 ml) is slowly added to the supernatant fraction (with stirring) to bring the ammonium sulphate concentration to 30%, a concentration that will effectively precipitate the reductase enzyme. Following 30 additional min. of stirring, the suspension is centrifuged at 26,000× g for 30 min., and the pellet resuspended in one tenth of the volume of the first supernatant fraction, S1, using a solution consisting of 25 mm HEPES, 1M NaCl, 1 mM DTT, 0.1 mM PMSF. The suspension is centrifuged at 100,000× g for one hour, and the resulting pellet resuspended in 25 mM HEPES, 10% glycerol (again at 1/10th of the S1 volume). Centrifugation of this suspension at 100,000× g yields the washed microsomal pellet, P4, which is resuspended in 1/20th of the S1 volume of 25 mM HEPES, 10% glycerol yielding a protein concentration of about 3–4 mg/ml. Aliquots are frozen at −70° C. for later use.

D. Study of Membrane Association of Reductase Activity

The Triton X114 phase fractionation procedure described by Bordier (J. Biol. Chem. (1981) 256:1604–1607) is used to determine whether the jojoba reductase is an integral membrane protein, or is more loosely associated with the membrane layer (more highly hydrophillic proteins). This technique essentially involves incubation of the membranes with 1% Triton X114 on ice followed by raising the temperature of the mixture above the cloud point of the detergent under these conditions (the cloud point is the temperature at which very large micelles begin to spontaneously form, for 1% Triton X114 this is ~20° C.). Upon centrifugation, two distinct phases can be observed, a lower detergent rich phase and an upper detergent depleted phase (refered to here as the aqueous phase). Integral membrane proteins have been shown to preferentially partition into the detergent rich phase while more highly hydrophilic proteins are recovered in the aqueous phase. When jojoba membrane preparations are subjected to this Triton X114 phase fractionation protocol, reductase activity is associated with the detergent enriched phase and no reductase activity is detected in the aqueous phase. This is evidence that the reductase enzyme is an integral membrane protein.

E. Further Characterization of Reductase Enzyme

The microsomal membrane preparation described above is used for further characterization of the reductase enzyme. The reductase enzyme was shown to be active over the range of pH 5–9. Characterization experiments were conducted at pH 7.5, which is close to the presumed physiological pH of the cytoplasm.

1. Salt Effects: A variety of salts were examined for their effect on reductase activity using a standard concentration of 0.5M for monobasic salts. Salts with divalent cations or anions were examined at 0.167M (to give the same ionic strength as the 0.5M monobasic salts) and also at 0.5M. Up to 15-fold stimulation is observed with the addition of 0.5M NaCl. Other salts, both monovalent and divalent (such as LiCl, KCl, $MgCl_2$, $CaCl_2$ and $Na_2SO_4$) were also shown to stimulate reductase activity, although generally to a lesser degree as compared to the NaCl stimulation. Strongly chaotropic salts, KSCN and NaSCN gave no stimulation or marginal stimulation of reductase activity.
2. Other Effectors: Dithiothreitol (DTT) was found to be stimulatory to reductase activity, but not obligatory, while ethylenediaminetetraacetic acid (EDTA) gave some stimulation, with the optimum concentration being 2.5 mM. A small stimulation of activity was observed at low (0.02–0.075 mg/ml) BSA (bovine serum albumin) concentrations, while inhibition of activity was observed at BSA concentrations at and above 0.2 mg/ml.

Earlier observations that the acyl-CoA reductase is an NADPH specific activity (Pollard et al., supra) were confirmed. No NADH-dependent activity was measurable above background (<2% of the NADPH-dependent activity). Also, both water-soluble end-products of the reductase reaction, CoA and NADP+, give significant inhibition of activity (at millimolar concentrations), while NADH and NAD+ have marginal effects on activity.

3. Substrate Specificity: The thioesters of various chain length fatty acids, acyl-ACPs and acyl-CoAs, were compared as substrates for the reductase enzyme. Tests were conducted at substrate concentrations of 10 uM, as the tetracosenoyl-CoA (24:1-CoA) substrate shows strong substrate inhibition at greater concentrations. NaCl concentration in these assays is 0.5M. Results of the substrate specificity experiment are presented in the Table below.

Table

| | Acyl Specificity of the Reductase | |
|---|---|---|
| | Reductase Activity (pmoles/min/μl) | |
| Acyl Group | Acyl-ACP (10 μM) | Acyl-CoA (10 μM) |
| 12:0 | <0.01 | <0.15 |
| 16:0 | 2.9 | <0.4 |
| 18:0 | — | 1.4 |
| 18:1 | 1.05 | 0.75 |
| 20:1 | — | 1.0 |
| 22:1 | — | 1.0 |
| 24:1 | — | 19.9 |

Tetracosenoyl-CoA has the highest substrate activity of those tested, and is thus used for reductase assays in further enzyme purification and characterization experiments. Of interest, palmitoyl-CoA (C16:0-CoA) and palmitoyl-ACP (C16:0-ACP) were directly compared as substrates. The activity towards palmitoyl-CoA was barely above background, while activity towards palmitoyl-ACP was high. Previously, stearoyl-ACP (C18:0-ACP) was shown to have activity as a substrate (Pollard et al., supra).

Also of interest, although palmitoyl-CoA appears to be a poor substrate for the reductase enzyme, in a competitive inhibition experiment conducted using unlabelled palmitoyl-CoA (0–30 μM) and [1-14C] tetracosenoyl-CoA (20 μM), 50% inhibition of reductase activity towards tetracosenoyl-CoA occurred at 5 μM palmitoyl-CoA. Thus, although palmitoyl-CoA is a poor substrate under the assay conditions, it is an effective inhibitor.

4. Reductase Inhibitor Assays: Several known inhibitors of other types of reductase proteins were tested for their effect on the jojoba acyl-CoA reductase activity. Mevinolin, which is a strong inhibitor of HMG-CoA reductase (3-hydroxyl-3-methylglutaryl-coenzymeA reductase), only had an effect at relatively high concentrations (100 uM) compared to the concentrations inhibitory to HMG-CoA reductase (Ki of approximately 1 nM). Cerulinen is well known to covalently bind to β-ketoacyl thioester synthases, but has no strong inhibitory effect on the jojoba acyl-CoA reductase.

Sulphydryl blocking agents were also screened for their effect on reductase activity. N-ethylmaleimide was shown to strongly inhibit activity, while para-hydroxymercuribenzoate also had some inhibitory effect, and iodoacetamide had no effect. This evidence leads to the conclusion that the acyl-CoA reductase has an essential sulphydryl group that shows considerable selectivity towards various sulphydryl blocking reagents.

Example 3

Purification of Acyl-CoA Reductase

Methods are described which may be used for isolation of a jojoba membrane preparation having reductase activity, solubilization of reductase activity and further purification of the reductase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 µg/ml leupeptin, 0.5 µg/ml pepstatin and 17 µg/ml PMSF. A cell free homogenate (CFH) is formed by dispersing the powdered embryos in the buffer with a Polytron tissue homogenizer for approximately 30 seconds. The homogenate is filtered through three layers of Miracloth (CalBioChem, LaJolla, Calif.) and the filtrate is centrifuged at 100,000× g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 1 mM EDTA. The dialyzate is centrifuged at 200,000× g for one hour to yield a pellet, DP2. The pellet is suspended in 25 mM HEPES (pH7.5), 10% (w/v) glycerol, 1 mM EDTA and 0.5M NaCl at approximately 1/20 of the original CFH volume, to yield the microsomal membrane preparation.

Activity is assayed as described in Example 1. Recovery of acyl-CoA reductase activity is estimated at approximately 30% of the original activity in the cell free homogenate. Acyl-CoA reductase activity in this preparation is stable when stored at ∼70° C.

B. Solubilization of Reductase Protein

Solid CHAPS (3-[(3-cholamidopropyl)-dimethylammonio] -1-propanesulfonate) is added to the microsomal membrane preparation to yield a final concentration of 2% (w/v). The sample is incubated on ice with a slow rocking motion for approximately one hour and then diluted with 25 mM HEPES (pH7.5), 10% glycerol, 0.34M NaCl, 1 mM EDTA to lower the CHAPS concentration to 0.75% and the NaCl to approximately 0.4M. The sample is then centrifuged at 200,000× g for one hour and the supernatant recovered and assayed for reductase activity as described in Example 1. Typically, 85% of the reductase activity from the microsomal membrane preparation is recovered in the supernatant fraction. The solubilized reductase activity is stable when stored at ∼70° C.

C. Blue A Column Chromatography

A column (1.8× ∼10 cm) with a bed volume of approximately 25 ml is prepared which contains Blue A (Cibacron Blue F3GA; Amicon Division, W. R. Grace & Co.), and the column is equilibrated with Buffer A (25 mM HEPES (pH7.5), 20% (w/v) glycerol, 0.75% CHAPS, 1 mM EDTA) containing 0.4M NaCl. The solubilized reductase preparation described above is loaded on to the Blue A column.

The column is washed with several column volumes of Buffer A containing 0.4M NaCl and is then washed further with Buffer A containing 0.5M NaCl. Greater than 90% of the reductase activity binds to the column, while greater than 85% of other protein passes through. Reductase activity is eluted from the column with Buffer A containing 1.0M NaCl. Fractions are collected and assayed for reductase activity as described in Example 1. Fractions containing reductase activity are pooled and stored at −70° C. Typically, 30–50% of the loaded reductase activity is recovered by elution with the 1.0M NaCl buffer.

D. Size Exclusion Chromatography

The pooled active fractions from the Blue A column are concentrated ∼10 fold via ultrafiltration in a pressure cell fitted with a YM30 membrane (Amicon Division, W. R. Grace). Typically, the activity is eluted from the Blue A column in ∼90 ml and concentrated to ∼8 ml and applied to two Sephacryl S100 columns as follows. Columns (2.5×75 cm) are packed with S100HR medium (Pharmacia LKB Biotechnology, Piscataway, N.J.) and equilibrated with Buffer A containing 0.5M NaCl. The columns are size calibrated with the following protein standards: bovine serum albumin (66 kD), carbonic anhydrase (29 kD), cytochrome C (12.4 kD), and blue dextran (used to determine the void volume). A four ml aliquot of the concentrated sample is applied to each of the S100 columns, which are developed at a linear flow rate of approximately 17 cm/hr. Fractions are collected for ∼4 hours and the reductase activity in the fractions is measured as described in Example 1.

Greater than 60% of loaded activity is recovered in one main peak which elutes at an apparent molecular mass of approximately 49 kD. The volume of the pooled active fractions is ∼30–35 ml/column.

E. Affinity Chromatography

A column (1.5 cm× ∼2 cm) is packed with palmitoyl-CoA agarose (Sigma Chemical Co., St. Louis, Mo.) and equilibrated with Buffer B (Buffer A containing 0.1M NaCl). Pooled active fractions from the gel filtration columns are concentrated ∼16 fold via ultrafiltration as described above. The NaCl level in the concentrated sample is reduced from 0.5M to ∼0.1M by dilution with Buffer A. The diluted sample is applied to the column which is then washed with several column volumes of Buffer B. The column is then washed with 10 ml of Buffer B containing 15 mM NADH, followed by further washing with Buffer B. Reductase activity is eluted by passing 15 ml of 15 mM NADPH in Buffer B through the column. Typically, the material from one gel filtration column at a time is processed on the affinity column, and greater than 70% of the activity applied to the column is recovered by elution with NADPH. The active fractions are pooled and analyzed for reductase activity, protein concentration and polypeptide composition. Protein concentrations are estimated using a commercially available kit (Bio-Rad Laboratories, Inc., Richmond, Calif.) based on the dye binding method described by Bradford (*Analy. Biochem.* (1976) 72:248–254). BSA is used as the reference protein.

F. SDS PAGE Analysis

Polypeptide composition of the sample is analyzed by SDS PAGE (Laemmli, U.K. (1970) *Nature* (London) 227:680–685). The samples are prepared for electrophoresis by adding SDS and dithiothreitol from stock solutions to a final concentration of 2% and 30 mM, respectively. Approximately 50 μl of the sample is loaded onto the well of an acrylamide gel having a 12% separating gel (NOVEX, San Diego, Calif.). Molecular mass standards were purchased from Bio-Rad Laboratories. Protein is detected by silver staining (Blum et al., *Electrophoresis* (1987) 8:93–99).

Two prominent polypeptide bands having apparent molecular masses of approximately 52 and 54 kD are detected in the active sample from the affinity column which together represent >95% of the protein in this preparation. As the apparent size of the reductase enzyme in the native state is approximately 49 kD (as determined by size exclusion chromatography and described above), these bands likely represent related forms of the reductase enzyme rather than two different subunits of one enzyme.

G. Blotting Proteins to Membranes

The above described reductase polypeptides are further isolated for amino acid sequencing by transfer of these proteins to either nitrocellulose or PVDF, either Immobilon-P (Millipore; Bedford, Mass.) or ProBlott (Applied Biosystems; Foster City, Calif.), membranes following SDS-PAGE. Nitrocellulose is preferred when proteins will be subsequently enzymatically digested, while PVDF is useful for N-terminal sequencing methods and for sequencing of peptides resulting from cyanogen bromide digestion.

1. Blotting to Nitrocellulose: When protein is electroblotted to nitrocellulose, the blotting time is typically 1–5 hours in a buffer such as 25 mM Tris, 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bags at ~20° C. If time permits, blots are not frozen but used immediately for digestion to create peptides for determination of amino acid sequence as described below.

2. Blotting to PVDF: When protein is electroblotted to Immobilon P PVDF, the blotting time is generally about 1–2 hours in a buffer such as 12.5 mM Tris/5 mM glycine in 10% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 4A.

Example 4

Determination of Amino Acid Sequence

In this Example, methods for determination of amino acid sequences of plant proteins associated with acyl-CoA reductase activity are described.

A. Cyanogen Bromide Cleavage of Protein and Separation of

Cyanogen bromide cleavage is performed on the protein of interest using the methodology described in the Probe-Design Peptide Separation System Technical Manual from Promega, Inc. (Madison, Wis.). The reductase proteins are blotted to a PVDF membrane as described above. Protein bands are cut from the blot, placed in a solution of cyanogen bromide in 70% (v/v) formic acid, and incubated in this solution overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 μl of HPLC grade water is then added to the dried peptides and the water removed by evaporation in a Speed-Vac (Savant, Inc., Farmingdale, N.Y.).

Peptides are separated using a Tris/Tricine SDS-PAGE system similar to that described by Schägger and von Jagow (*Anal. Biochem.* (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3X 2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Proteins blotted to nitrocellulose may be subjected to digestion with proteases in order to obtain peptides for sequencing. The method used is that of Aebersold, et al. (PNAS (1987) 84:6970). Bands of the reductase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis. in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing. These two modifications eliminate interference problems with the PVP-40.

The pieces are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5-10% (v/v). Protease are diluted in digest buffer and added to the digest mixture, typically at a ratio of 1:10 (w/w) protease to protein. Digests are incubated 18-24 hours. For example, trypsin digests are incubated at 37° C. and endoproteinase gluC digests are incubated at room temperature. Similarly, other proteases may be used to digest the reductase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 $\mu$l 10% (v/v) trifluoroacetic acid (TFA) or 1 $\mu$l 100% TFA. The digest mixture is removed from the nitrocellulose pieces, the nitrocellulose pieces are washed with 1-5 100 $\mu$l volumes of digest buffer with 5-10% acetonitrile, and these volumes are concentrated to a volume of less than 100 $\mu$l in a Speed-Vac. The peptides are separated on a Vydac reverse phase C18 column (2.1 mm×100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH2.2; Buffer B: 70% acetonitrile in 0.1 mM sodium phosphate, pH2.2. A 3-step gradient of 10-55% buffer B over two hours, 55-75% buffer B over 5 minutes, and 75% buffer B isocratic for 15 minutes at a flow rate of 50 $\mu$l/minute is used. Peptides are detected at 214 nm, collected by hand, and then stored at $-20°$ C.

C. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using AC-CESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5-30 pmoles), the 477A conversion cycle and the 120A analyzer as described by Tempst and Riviere (*Anal. Biochem.* (1989) 183:290).

Example 5

Jojoba cDNA Library

Construction of jojoba embryo cDNA libraries from poly(A)+RNA isolated from jojoba embryos collected at 80-90 days post-anthesis is described.

A. Jojoba RNA Isolation

RNA is isolated from polyribosomes by a method initially described by Jackson and Larkins (*Plant Physiol.* (1976) 57:5-10) as modified by Goldberg et al. (*Developmental Biol.* (1981) 83:201-217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 05% sodium deoxycholate, 1 mM spermidine, 10 mM $\beta$-mercaptoethanol, and 500 mM sucrose) is added and the tissue is homogenized for about 2 minutes. The homogenate is filtered through sterile miracloth and centrifuged at 12,000× g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000× g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM $\beta$-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM MgCl2, 5 mM $\beta$-mercaptoethanol) is added to each tube. The tubes are placed on ice for 10 minutes, after which the pellets are thoroughly resuspended and pooled. The supernatant is then centrifuged at 120× g for 10 minutes to remove insoluble material. One volume of self-digested 1 mg/ml proteinase K in 20 mM Tris pH 7.6, 200 mM EDTA, 2% N-lauryl-sarcosinate is added to the supernatant and the mixture incubated at room temperature for 30 minutes.

RNA is precipitated by adding 1/10 volume of sodium acetate and 2 volumes of ethanol. After several hours at $-20°$ C. RNA is pelleted by centrifugation at 12,000× g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000× g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

B. cDNA Library Construction in a Plasmid Vector

Polyadenylated RNA is used to construct a cDNA library in the plasmid cloning vector pCGN1703, derived from the commercial cloning vector Bluescribe M13-(Stratagene Cloning Systems; San Diego, Calif.), and made as follows. The polylinker of Bluescribe M13 is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and Sinai, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into E. coli strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

C. cDNA Library Construction in a Lambda Vector

Jojoba polyadenylated RNA is also used to construct a cDNA library in the cloning vector λZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations.

The cDNA library constructed in this manner contins approximately $1 \times 10^6$ clones with an average cDNA insert size of approximately 400 base pairs.

The above results demonstrate the ability to obtain solubilized seed-plant fatty acyl reductase protein which is active in the formation of a fatty alcohol. Methods to obtain the acyl reductase protein and amino acid sequences thereof are provided. In addition, methods to obtain reductase nucleic acid sequences from the amino acid sequences are also provided. These nucleic acid sequences may be manipulated to provide for transcription of the sequences and/or expression of reductase proteins in host cells, which proteins may be used for a variety of applications.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A partially purified jojoba embryo fatty acyl-CoA reductase consisting essentially of said reductase having a molecular mass of about 53 kD wherein said reductase catalyzes the reduction of a fatty acyl substrate to the corresponding alcohol and wherein said reductase is NADPH-dependent.

2. The reductase of claim 1 having activity toward a fatty acyl-CoA substrate or a fatty acyl-ACP substrate.

3. The reductase of claim 2 wherein the carbon chain of said fatty acyl-CoA has the formula $C_{2x}$ wherein X is selected from the group 8–12, and wherein said carbon chain is unsaturated, or is mono-unsaturated.

* * * * *